US011185271B2

(12) United States Patent
Negi et al.

(10) Patent No.: US 11,185,271 B2
(45) Date of Patent: Nov. 30, 2021

(54) METHODS OF MAKING MICRO-MOLDED ELECTRODES AND ARRAYS

(71) Applicant: University of Utah Research Foundation, Salt Lake City, UT (US)

(72) Inventors: Sandeep Negi, Salt Lake City, UT (US); Rajmohan Bhandari, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1632 days.

(21) Appl. No.: 15/021,858

(22) PCT Filed: Sep. 12, 2014

(86) PCT No.: PCT/US2014/055515
§ 371 (c)(1),
(2) Date: Mar. 14, 2016

(87) PCT Pub. No.: WO2015/038974
PCT Pub. Date: Mar. 19, 2015

(65) Prior Publication Data
US 2016/0220135 A1 Aug. 4, 2016

Related U.S. Application Data

(60) Provisional application No. 61/877,695, filed on Sep. 13, 2013.

(51) Int. Cl.
*A61N 1/05* (2006.01)
*A61B 5/24* (2021.01)
(Continued)

(52) U.S. Cl.
CPC ............... *A61B 5/24* (2021.01); *A61B 5/291* (2021.01); *A61B 5/296* (2021.01); *A61B 5/389* (2021.01);
(Continued)

(58) Field of Classification Search
CPC ... A61B 5/04001; A61B 5/0478; A61B 5/685; A61B 2562/125; A61B 5/24;
(Continued)

(56) References Cited

U.S. PATENT DOCUMENTS 5,002,651 A    3/1991  Shaw et al.
5,591,139 A *  1/1997  Lin ................... A61M 37/0015
                                              604/264

(Continued)

FOREIGN PATENT DOCUMENTS

WO    WO 2011/105665 A1    9/2011
WO    WO 2012/046149       4/2012
WO    WO 2013/061208       5/2013

OTHER PUBLICATIONS

Stieglitz et al.; "Flexible BIOMEMS with electrode arrangements on front and back side as key component in neural prostheses and biohybrid systems"; Sensors and Actuators B—Chemical; 2002; p. 8-14; vol. 83, No. 1-3; Elsevier.

(Continued)

*Primary Examiner* — Peter Dungba Vo
*Assistant Examiner* — Kaying Kue
(74) *Attorney, Agent, or Firm* — Thorpe North & Western, LLP.

(57) ABSTRACT

A method of manufacturing a micro-molded electrode (160) having multiple individually addressable sensors (140) along a shaft (180) can include forming a recess in a mold substrate, depositing a structural material therein, depositing a conductive material at specific locations, providing a coating (190), and removing the mold substrate. A micro-molded electrode (160) having a base (170) tapering to at least one shaft (180) can include an electrode substrate, multiple individually addressable sensors (140), and a coating (190).

17 Claims, 13 Drawing Sheets

(51) Int. Cl.
*A61B 5/00* (2006.01)
*A61B 5/291* (2021.01)
*A61B 5/296* (2021.01)
*A61B 5/389* (2021.01)

(52) U.S. Cl.
CPC .......... *A61B 5/4029* (2013.01); *A61B 5/4058* (2013.01); *A61B 5/685* (2013.01); *A61N 1/0551* (2013.01); *A61B 2562/125* (2013.01)

(58) Field of Classification Search
CPC ..... A61B 5/4029; A61B 5/4058; A61B 5/291; A61B 5/296; A61B 5/389; A61N 1/0551; H05K 3/1258; H05K 3/12; Y10T 29/49155; Y10T 29/49158; Y10T 29/4916
USPC .......... 29/849, 846, 829, 852, 884, 885, 883
See application file for complete search history.

(56) References Cited

U.S. PATENT DOCUMENTS

| | | | |
|---|---|---|---|
| 6,256,533 B1 | 7/2001 | Yuzhakov et al. | |
| 6,312,612 B1 | 11/2001 | Sherman et al. | |
| 6,334,856 B1 | 1/2002 | Allen et al. | |
| 6,471,903 B2 | 10/2002 | Sherman et al. | |
| 6,503,231 B1 | 1/2003 | Prausnitz et al. | |
| 6,551,849 B1 | 4/2003 | Kenney | |
| 6,565,532 B1 | 5/2003 | Yuzhakov et al. | |
| 6,652,478 B1 | 11/2003 | Gartstein et al. | |
| 6,743,211 B1 | 6/2004 | Prausnitz et al. | |
| 6,961,603 B2 * | 11/2005 | Merilainen | A61B 5/04085 600/383 |
| 7,212,851 B2 * | 5/2007 | Donoghue | A61B 5/04001 600/378 |
| 7,344,499 B1 | 3/2008 | Prausnitz et al. | |
| 7,416,541 B2 | 8/2008 | Yuzhakov et al. | |
| 7,763,203 B2 | 7/2010 | Arias et al. | |
| 7,946,050 B2 * | 5/2011 | Chiou | G01R 1/07321 324/754.07 |
| 8,255,061 B2 * | 8/2012 | Perlin | A61N 1/0529 607/116 |
| 8,257,324 B2 | 9/2012 | Prausnitz et al. | |
| 8,261,428 B2 * | 9/2012 | Fang | A61B 5/0478 29/592.1 |
| 8,308,960 B2 | 11/2012 | Kalvesten et al. | |
| 9,403,011 B2 * | 8/2016 | Mercanzini | A61N 1/37229 |
| 9,925,376 B2 * | 3/2018 | Hartig | A61N 1/0551 |
| 2002/0038509 A1 * | 4/2002 | Soejima | H05K 3/3436 29/843 |
| 2002/0082543 A1 * | 6/2002 | Park | A61N 1/30 604/21 |
| 2003/0135158 A1 | 7/2003 | Gonnelli | |
| 2004/0200063 A1 * | 10/2004 | Thurgood | H01L 23/13 29/830 |
| 2004/0260166 A1 * | 12/2004 | Merilainen | A61B 5/0478 600/383 |
| 2006/0276866 A1 | 12/2006 | McCreery | |
| 2008/0063866 A1 | 3/2008 | Allen et al. | |
| 2008/0249391 A1 | 10/2008 | Moxon et al. | |
| 2009/0306454 A1 | 12/2009 | Cockerham et al. | |
| 2010/0010601 A1 | 1/2010 | Negi et al. | |
| 2010/0029148 A1 * | 2/2010 | Perlin | A61N 1/0529 439/884 |
| 2010/0193997 A1 | 8/2010 | Frederickson et al. | |
| 2010/0287770 A1 * | 11/2010 | Dadd | A61N 1/0541 29/877 |
| 2011/0071596 A1 * | 3/2011 | Kara | B82Y 30/00 607/57 |
| 2011/0125001 A1 * | 5/2011 | Fang | A61B 5/0478 600/372 |
| 2011/0177978 A1 | 7/2011 | Luo et al. | |
| 2011/0270221 A1 | 11/2011 | Ross | |
| 2011/0276003 A1 | 11/2011 | Luttge et al. | |
| 2011/0306853 A1 | 12/2011 | Black et al. | |
| 2013/0046148 A1 * | 2/2013 | Tathireddy | A61N 1/0551 600/300 |
| 2013/0131482 A1 | 5/2013 | Fedder et al. | |
| 2013/0333918 A1 * | 12/2013 | Lotfi | B29C 48/12 174/117 R |

OTHER PUBLICATIONS

PCT Application No. PCT/US2014/055515; Filing date Sep. 12, 2014, Rajmohan Bhandari, International Search Report, dated Dec. 22, 2014, 10 pages.
Hajj-Hassan et al., Reinforced Silicon Neural Microelectrode Array Fabricated Using a Commercial MEMS Process, J. Micro/Nanolith, MEMS MOEMS, vol. 8(3), Jun. 2, 2009, 033011-1-033011-8.
Choi et al., 3-D Patterned Microstructures Using Inclined UV Exposure and Metal Transfer Micromolding, www.researchgate.net, https://researchgate.net/publication/237437113_3-D_Patterned_Microstructures_Using_Inclined_UV_Exposure_and_Metal_Transfer_Micromolding, Accessed on Oct. 27, 2016, 4 Pages.
Choi et al., An Electrically Active Microneedle Array for Electroporation, Biomed Microdevices, vol. 12 (2), Apr. 2010, 263-273.
Choi et al., Intracellular Protein Delivery and Gene Transfectino by Electroporation Using a Microneedle Electrode Array, Small, vol. 8 (7), Apr. 10, 2012, 1081-1091.
Fager, Andrew, Development and Fabrication of High Aspect Ratio Out of Plane Microchannels for Use in Microneedle Applications, Department of Electrical and Computer Engineering, University of Utah, Aug. 2008, 71 pages.
Kim et al., Mironeedles for Drug and Vaccine Delivery, Advanced Drug Delivery Reviews, vol. 64, May 1, 2012, 1547-1568, Elsevier.
Merlo et al., Microelectrode Arrays Fabricated Using a Novel Hybrid Microfabrication Method, Biomed Microdevices, vol. 14(1), Feb. 2012, 193-205.
Nguyen et al., Design, Fabrication and Characterization of Drug Delivery Systems Based on Lab-On-A-Chip Technology, Advanced Drug Delivery Reviews, vol. 65, Issues 11-12, Nov. 15, 2013, 1403-1419, Elsevier.
Noh et al., Parylene Micromolding, a Rapid and Low-Cost Fabrication Method for Parylene Microchannel, Sensors and Actuators, vol. 102, Sep. 20, 2003, 78-85, Elsevier.
Rajaraman et al., Micromachined Three-Dimensional Electrode Arrays for Transcutaneous Nerve Tracking, J. Micromech. Microeng., vol. 21, Jun. 30, 2011, 14 pages.
Wang et al., Hollow Polymer Microneedle Array Fabricated by Photolithography Process Combined with Micromolding Technque, Conf Proc IEEE Eng Med Biol Soc., Nov. 13, 2009, 7026-7029.
Zhou et al, Fabrication of Pyramid-Shaped Three-Dimmensional Flexible Microelectrode Array for Improved Neural Interfacing, American Scientific Publishers, vol. 7 Issue 1, Feb. 1, 2009, pp. 102-109(8).

* cited by examiner

METHODS OF MAKING MICRO-MOLDED ELECTRODES AND ARRAYS

RELATED APPLICATION

This application claims the benefit of U.S. Provisional Application No. 61/877,695, filed Sep. 13, 2013, which is incorporated herein by reference.

GOVERNMENT INTEREST

This invention was made with government support under R43 NS073162 awarded by the National Institutes of Health. The government has certain rights in the invention.

FIELD OF THE INVENTION

The present invention relates generally to microelectrodes, arrays thereof, and methods of fabrication. Accordingly, the present invention involves the fields of microscale fabrication, materials science, and process control.

BACKGROUND

In the last two decades, the field of neuroprosthetics has gained tremendous momentum through the development of novel architectures for neural interfaces. However, to date, there is no device that has been identified as the "gold standard" in the field. As a result, the research and technology environment for neural interfaces is still highly limited. This is due to the constant need and desire to have electrodes and interconnections designed and developed according to unique specifications suited to a particular application, physiological approach, animal model, or variety of other concerns. Hence, the requirements of each laboratory are typically unique and require a high-level of customization and integration.

For example, microelectrode arrays can be used to stimulate and record electrical neuronal signals in the central nervous system (CNS) and peripheral nervous system (PNS). Sensory organs generate electrical signals that are transmitted by nerves to the brain. Nerves also conduct electrical signals from the brain to control muscular activity. Microelectrodes can be inserted into nerve tissue to record and stimulate electrical signals in various parts of the nerve tissue.

The pursuits of researchers are often limited by technological limitations, inadequate resources, infrastructure and insufficient budget. Hence researchers feel handicapped as none of the micro devices (penetrating or surface) currently in the market are fully customizable (e.g. with respect to probe geometrical parameters and substrate material), sufficiently reliable, and, most importantly, affordable on a cost-conscience budget. Such limitations hamper a researcher's ability to pursue their scientific quest to validate their hypothesis and, hence, delay potential clinical applications. Therefore, there is still a great need for further research and development of improved neural interfaces.

SUMMARY OF THE INVENTION

The present technology is directed to micro-molded electrodes, arrays thereof, and methods of fabricating such electrodes and arrays. The present electrodes and devices have customizable dimensions, e.g., lengths, and can have high aspect ratios.

In one embodiment, a method of manufacturing a micro-molded electrode having multiple individually addressable sensors along a shaft of the electrode is described. This method can include modifying a mold substrate to form a recess therein on a first surface of the mold substrate. The recess defines a perimeter of the electrode. The method also includes depositing a structural material within the recess to form the micro-molded electrode. Further, a conductive material can be deposited at specific locations on the micro-molded electrode such that the conductive material forms the multiple individually addressable sensors along the shaft of each micro-molded electrode. More specifically, each sensor comprises a bonding pad at a base of the micro-molded electrode electrically connected to an active site on the shaft of the electrode via an electrically conductive trace. The micro-molded electrode has an active site on at least two sides of the micro-molded electrode. The method also includes coating a top side of the micro-molded electrode and at least one trace with a coating material; and removing the mold substrate outside the perimeter.

In another embodiment, a micro-molded electrode having a base tapering to at least one shaft is described. This micro-molded electrode can include an electrode substrate having multiple individually addressable sensors on at least one side of the electrode substrate. Also, each individually addressable sensor can include a bonding pad at the base of the micro-molded electrode which is electrically connected to an active site on the shaft of the micro-molded electrode via an electrically conductive trace. The micro-molded electrode has an active site on at least two sides of the micro-molded electrode; and a coating covering a first side of the micro-molded electrode including at least one trace. Optionally, a plurality of micro-molded electrodes can be combined in 2D or 3D arrays.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

Figure 1A:
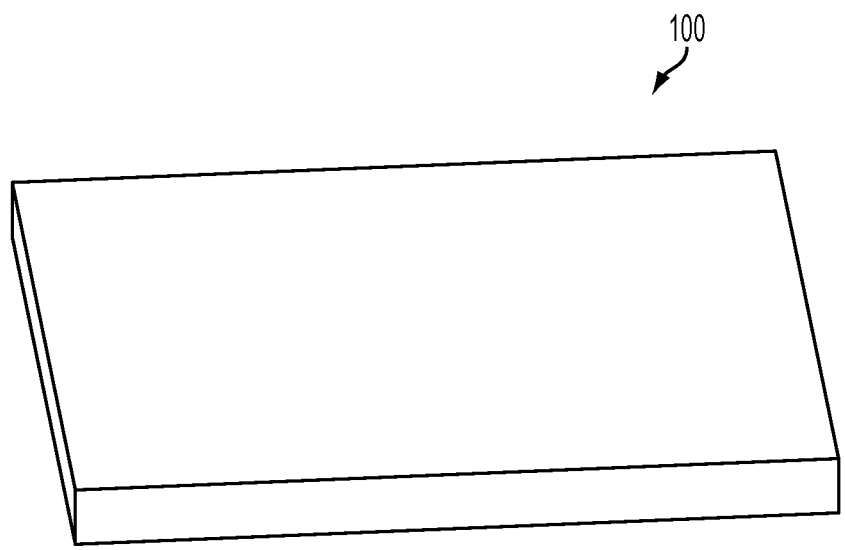
FIG. 1A is a perspective view of a mold substrate in accordance with an embodiment of the present disclosure.

These drawings merely depict exemplary embodiments of the present invention they are, therefore, not to be considered limiting of its scope. It will be readily appreciated that the components of the present invention, as generally described and illustrated in the figures herein, could be arranged, sized, and designed in a wide variety of different configurations. Nonetheless, the invention will be described and explained with additional specificity and detail through the use of the accompanying drawings.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and "the" include plural referents unless the context clearly dictates otherwise. Thus, for example, reference to "a channel" includes one or more of such particles, reference to "layers" includes reference to one or more of such layers, and reference to "coating" includes one or more of such steps.

Definitions

In describing and claiming the present invention, the following terminology will be used in accordance with the definitions set forth below.

As used herein, "substantial" when used in reference to a quantity or amount of a material, or a specific characteristic thereof, refers to an amount that is sufficient to provide an effect that the material or characteristic was intended to provide. Therefore, "substantially free" when used in reference to a quantity or amount of a material, or a specific characteristic thereof, refers to the absence of the material or characteristic, or to the presence of the material or characteristic in an amount that is insufficient to impart a measurable effect, normally imparted by such material or characteristic.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, "at least one of" is meant to include at least one member of a referenced group, list, or the like, but can include more than one member of the group, list, or the like, in any combination. As a non-limiting example, "at least one of A, B, and C" can include only A, only B, only C, or any combinations of A, B, and C, such as A and B only, A and C only, B and C only, or A, B, and C together.

As used herein, "micro-molded electrode" refers to an electrode body or electrode substrate (e.g. electrically insulating materials) having at least one individually addressable sensor coupled to, deposited on, or otherwise connected to the electrode body or electrode substrate. However, a "micro-molded electrode" may also include numerous additional features as well, such as protective coatings, multiple sensors or sensor types, a channel or channels for delivery of a therapeutic agent or agents, a channel or channels for delivering electromagnetic radiation, other channels, and any other suitable features contemplated in designing a "micro-molded electrode."

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.6 mm to about 0.3 mm" should be interpreted to include not only the explicitly recited values of about 0.6 mm and about 0.3 mm, but also include individual values and sub-ranges within the indicated range. Thus, included in this numerical range are individual values such as 0.4 mm and 0.5, and sub-ranges such as from 0.5-0.4 mm, from 0.4-0.35, etc. This same principle applies to ranges reciting only one numerical value. Furthermore, such an interpretation should apply regardless of the breadth of the range or the characteristics being described.

As used herein, the term "about" means that dimensions, sizes, formulations, parameters, shapes and other quantities and characteristics are not and need not be exact, but may be approximated and/or larger or smaller, as desired, reflecting tolerances, conversion factors, rounding off, measurement error and the like and other factors known to those of skill in the art. Further, unless otherwise stated, the term "about" shall expressly include "exactly," consistent with the discussion above regarding ranges and numerical data.

In the present disclosure, the term "preferably" or "preferred" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Embodiments of the Invention

The present inventors have recognized a need in the neuroscience community to have technology that can provide customizable and affordable devices so that statistically relevant numbers of neural devices are available for engineering and physiological tests that can allow researchers to generate a pool of data to validate their hypotheses. Currently there is a wide range of commercially available microelectrode microsystems for both acute and chronic applications. However, most devices currently available on the market have various limitations. For example, probes provided by Neuronexus Technologies Inc., offer customization in electrode design to a certain extent, however the electrodes can (1) be fragile and hence prone to breakage during handling and insertion, (2) have sharp longitudinal edges along the probe, which tend to tear the tissue during insertion, (3) have cumbersome 3D integration of single probes and poor reliability of the 3D array in chronic use, (4) lack choice of substrate material, and (5) have a high cost for customized probes (as inherited from a tedious fabrication process which is a several mask process).

The mechanical, geometric, and electrical characteristics of micro-molded electrodes (MME) according to aspect of the invention are precise and highly reproducible for consistent, high-quality results. The current MME technology offers high-quality, high-channel count neural probes for single-unit, multi-unit and local field potential recording, electrical stimulation. The current invention can be used to produce both surface and penetrating electrodes from a wide variety of materials. Additionally, the shape is highly customizable with the option to have multiple active sides on both the top and bottom of the electrode. Furthermore, the electrode can have rounded edges for safer insertion and can be manufactured at a relatively low cost. Furthermore, the current technology provides substantial freedom to design electrodes to explore variables such as electrode material, shape, size, number, location of the active site, and any other suitable variables.

Accordingly, micro-molded electrodes and associated methods are described herein that can provide a plurality of benefits over the state of the art. In one embodiment, a method is described for manufacturing a micro-molded electrode having multiple individually addressable sensors along a shaft of the micro-molded electrode. This can include modifying a mold substrate to form a recess therein on a first surface of the mold substrate, the recess defining the perimeter of the micro-molded electrode. A structural material can be deposited within the recess to form the micro-molded electrode. A conductive material can be deposited at specific locations on the micro-molded electrode such that the conductive material forms the multiple individually addressable sensors along the shaft of each micro-molded electrode, each sensor including a bonding pad at a base of the micro-molded electrode electrically connected to an active site on the shaft of the micro-molded electrode via an electrically conductive trace. The micro-molded electrode can have an active site on at least two sides of the micro-molded electrode. A top side of the micro-molded electrode and at least one trace can be coated with a coating material. The mold substrate can be removed outside the perimeter. As used herein, "perimeter" refers to the portion of the substrate that delineates the deposited and coated materials from the remainder of the substrate in the horizontal plane but does not necessarily refer to the portion of the substrate extending in the vertical plane, viewing the electrode where length of the electrode (base to tip) is in the horizontal plane. As such, the substrate material on the bottom of the electrode (viewing the electrode laying on a surface—horizontal plane) is not necessarily excluded by the perimeter. However, in one embodiment, such substrate material can be excluded by the perimeter, or a portion of such substrate material can be excluded.

As further illustrated in FIGS. 1A-1F, this embodiment of fabricating micro-molded electrodes (MME) or micromolded arrays (MMA) is based on a platform technology and uses a novel micro molding technique which allows fabrication of surface and penetrating electrodes. As illustrated in FIG. 1A, this embodiment can use a mold substrate, generally depicted as 100. The mold substrate 100 can include any substrate that is modifiable to form a recess therein and can be made from any suitable material. In one aspect, the mold substrate can be made from at least one of silicon, silicon dioxide, silicon nitride, glass, quartz, aluminum, molybdenum, gold, chromium, platinum, tantalum, titanium, titanium nitride, tungsten, gallium arsenide, indium tin oxide, steel, polymers such as parylene-C, polyimide, PMMA, PDMS, photoresist materials, any other suitable material, and combinations thereof.

Figure 1B:
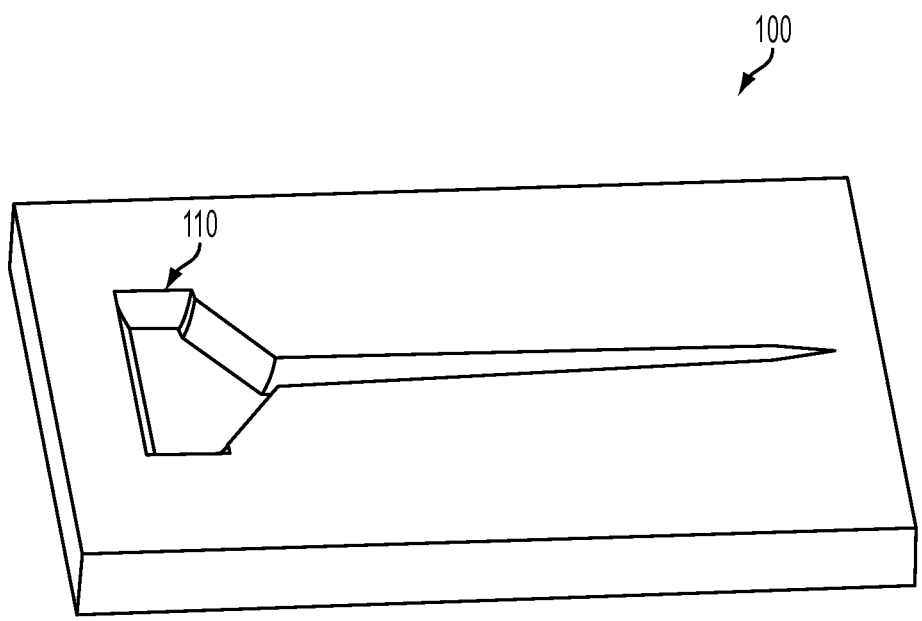
FIG. 1B is a perspective view of a mold substrate modified to include a recess in accordance with an embodiment of the present disclosure.
Figure 1C:
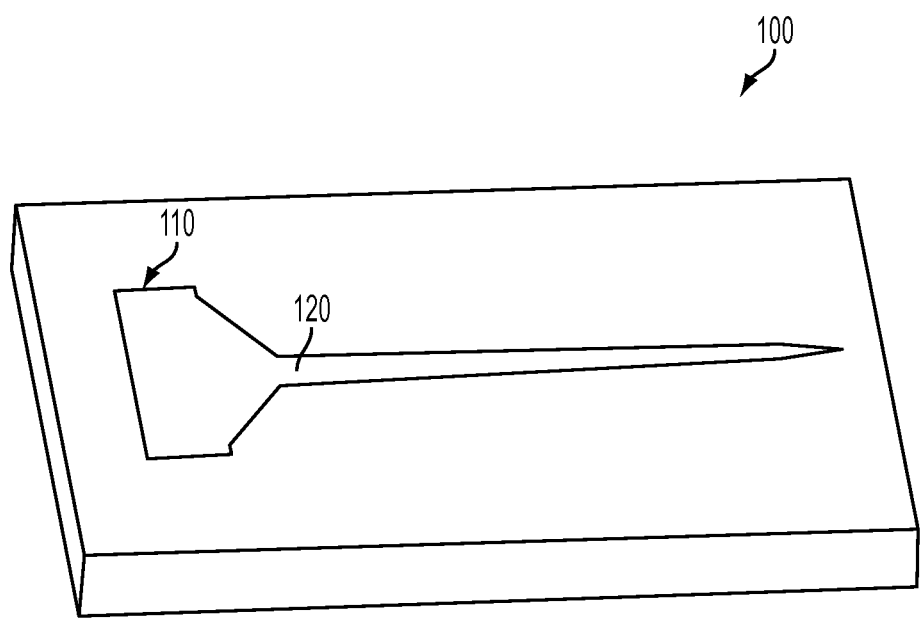
FIG. 1C is a perspective view of a mold substrate illustrating the recess of FIG. 1B filled with a structural material in accordance with an embodiment of the present disclosure.

Once an appropriate mold substrate 100 is selected, the mold substrate 100 can be modified in any suitable way to form a recess 110 within the mold substrate as depicted in FIG. 1B. In one aspect, the mold substrate 100 can be modified to from a recess 110 by compressing, carving, etching, burning, or otherwise modifying the mold substrate 100. In one aspect, the modification can be made by any suitable etching technique, such as wet or dry etching, anisotropic or isotropic etching, or any other etching process. In one aspect, the recess 110 can be formed using a process selected from the group consisting of reactive ion etching, deep reactive ion etching, wet chemical etching using etchants like KOH, HF, nitric acid, TMAH, EDP, and combinations thereof. In one specific aspect, deep reactive ion etching is used to produce the recess 110 in the mold substrate 100. Deep reactive ion etching can be a very desirable etching process in the current embodiment because of its ability to generate rounded edges for safer insertion of the micro-molded electrode. In one specific aspect, deep reactive ion etching can be used to produce a recess 110 of a depth from about 15 µm to about 300 µm deep within a 500 µm thick mold substrate. Similarly, the recess can be sized to form a particular shaft and base geometry. Although a wide variety of geometries can be used, typically the recess can be from about 10 µm to about 150 mm long and about 10 µm to 150 mm wide.

Figure 2:
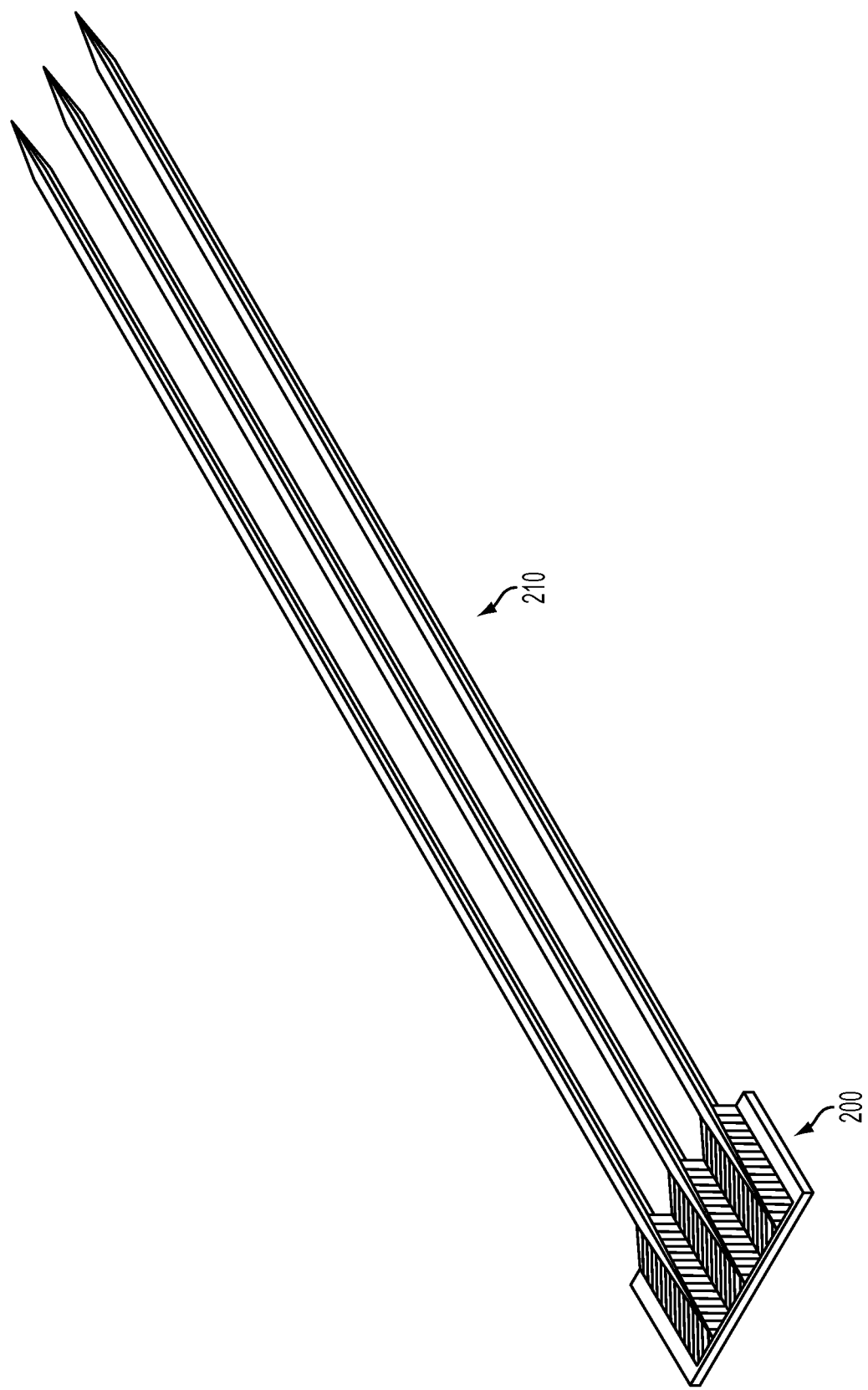
FIG. 2 is a perspective view of a micro-molded electrode with multiple shafts in accordance with an embodiment of the present disclosure.
Figure 3:
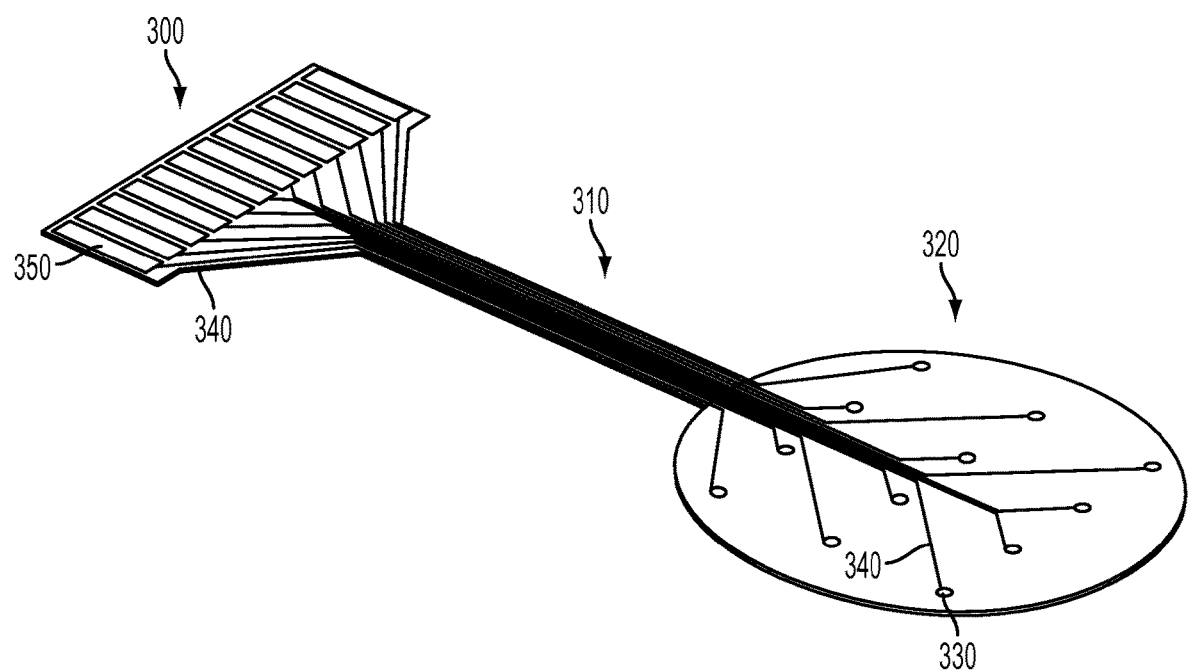
FIG. 3 is a perspective view of a surface micro-molded electrode in accordance with an embodiment of the present disclosure.

The recess 110 can have any suitable shapes, geometries, and dimensions within the confines of the mold substrate 100. For example, the recess 110 can be configured for production of a single shaft MME, a multiple shaft MME as shown in FIG. 2, an insertable MME, a surface MME as shown in FIG. 3, 3D arrays, or any other suitable configuration.

Referring back to FIG. 1C, a structural material 120 can be inserted into the recess 110 of the mold substrate. The structural material can be deposited in the recess using any suitable technique such as, but not limited to, powder consolidation, pouring molten material, spin coating, spray coating, sputtering deposition, e-beam evaporation deposition, and the like.

MMEs are defined by the structural material 120 used to fabricate them. For example, an MME made with glass is designated Glass MME, or an MME made with glass-polymer is designated Glass-PI MME. Although Glass MME and Glass-PI MME are commonly used, any suitable material can be used to produce MMEs. Some example materials can include, but are not limited to, silicon, aluminum, alumina, glass, quartz, steel, acrylics, silicon on insulator materials, polymeric materials such as parylene-C, polydimethylsiloxane (PDMS), and poly(methyl methacrylate) (PMMA), epoxy-based negative resist materials, such as SU8, ceramics, such as silicon carbide and tungsten carbide, and zinc oxide, and combinations thereof. In one aspect, the MME can be made from a structural material selected from the group consisting of silicon, aluminum, alumina, glass, quartz, steel, epoxy-based negative resist materials, acrylics, silicon on insulator (SOI), and combinations thereof. In one specific aspect, glass powder can be used to fill the recess 110 of the mold substrate 100. Additionally, other materials can be added to the structural material to provide added mechanical strength. Such materials can include steel, titanium, glass, quartz, and any other suitable material. In the case of a Glass-PI MME, a thin layer of glass can be added as a backbone to provide sufficient mechanical strength for insertion. This thin support layer can generally range from about 10 µm to about 500 µm in thickness.

Once a suitable structural material 120 has been added to the recess 110, the mold substrate 100 containing the structural material 120 can be heated, cooled, pressurized, exposed to electromagnetic radiation, or otherwise manipulated to form a solid cohesive structural material. Temperatures, pressures, exposure times, and other considerations for forming a solid cohesive structural material will vary according to the structural material selected for a given application, and are generally known by one skilled in the art. In one specific example, where glass powder is used as the structural material, the mold substrate 100 containing the structural material 120 can be placed in the oven at 1100 C for 6 hours to produce a solid cohesive structural material. The mold substrate 100 and solid cohesive structural material 120 can optionally be lapped and polished.

Figure 1D:
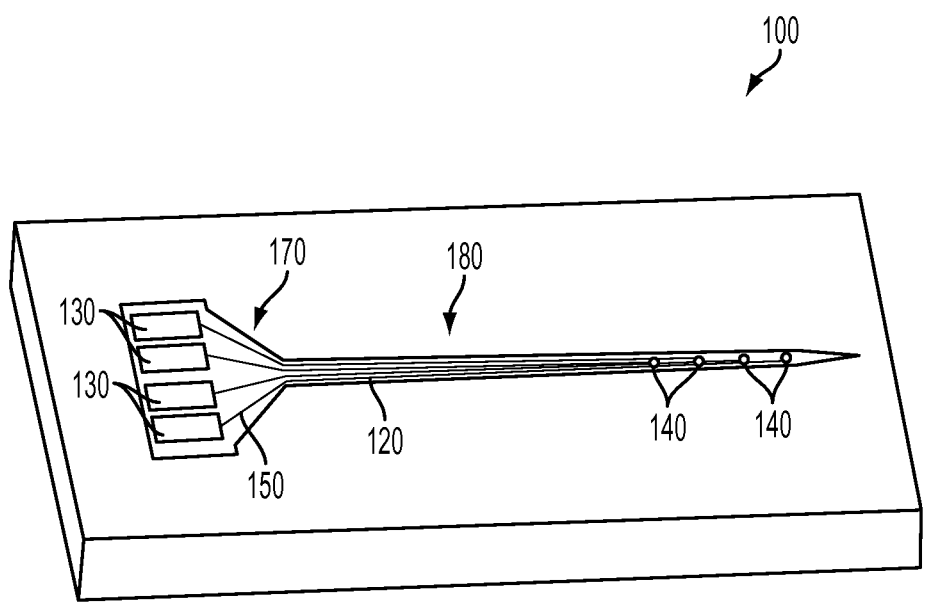
FIG. 1D is a perspective view of a mold substrate and structural material including the individually addressable sensors associated with the micro-molded electrode in accordance with an embodiment of the present disclosure.
Figure 1E:
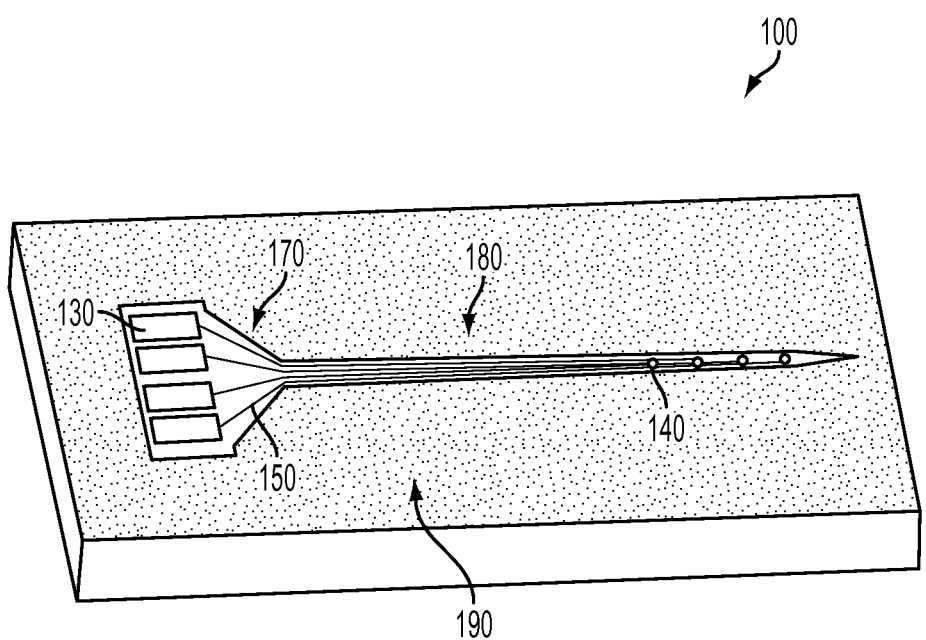
FIG. 1E is a perspective view of the micro-molded electrode of FIG. 1D with a coating in accordance with an embodiment of the present disclosure.

As shown in FIGS. 1D-1E, conductive material can be deposited and patterned as part of the micro-molded electrode. The deposited conductive materials can form individually addressable sensors along the shaft 180 of each MME. Each sensor can include a bonding pad 130 at the base 170 of the MME that is electrically connected to an active site 140 on the shaft 180 via an electrically conductive trace 150. The MME can have an active site 140 on at least two sides of the MME.

The conductive material can be deposited and patterned using any suitable deposition and patterning techniques. In one aspect, the conductive material can be DC sputtered and patterned using lithography. Deposition can be done by e-beam evaporation deposition, electroplating, electroless plating, and the like. Patterning can be done by lift-off technique also, or by laser.

Any suitable conductive material can be used to form the conductive components of the MME. In one aspect, platinum, gold, copper, titanium, silver, conductive polymers, iridium, aluminum, and combinations thereof can be used as the conductive material. In one specific aspect, platinum can be used.

As noted previously, the micro-molded electrode can have active sites on at least two sides of the MME. In one aspect, the structural material 120 can be deposited within the recess 110 after the deposition of conductive material within the recess 110. In another aspect, the structural material can be deposited within the recess 110 before the deposition of the conductive material. In this case, the conductive material can be deposited after the MME is removed from the mold substrate 100, or a channel can be formed within or on the periphery of the MME that allows an electrically conductive trace 150 to penetrate to or connect with an opposite or adjacent side.

A bonding pad 130 can be located on at least one side of the MME. In one aspect, at least one bonding pad 130 can be connected to an active site 140 on an opposite or adjacent side of the MME. This can be accomplished by providing a channel from one side of the MME to an opposite or adjacent side, the channel containing sufficient conductive material to form an electrically conductive trace 150 or segment of an electrically conductive trace that electrically connects the bonding pad 130 to the active site on the opposite or adjacent side of the MME. The channel can penetrate through the MME or it can be formed entirely on the periphery of the MME. In another aspect, at least one bonding pad 130 can be deposited on at least two sides of the MME. The bonding pads can be electrically connected to active sites on the same side or on opposite or adjacent sides to the sides where the bonding pads are located.

Figure 4:
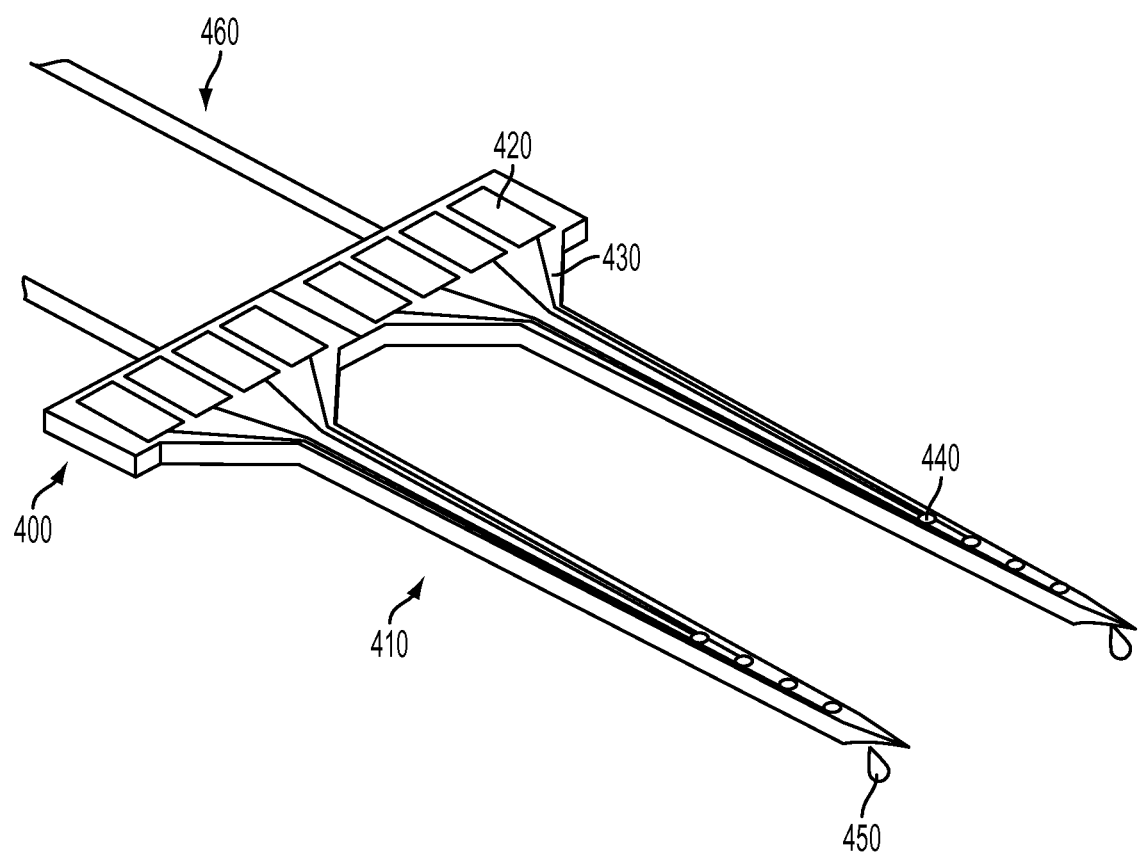
FIG. 4 is a perspective view of a micro-molded electrode adapted for delivery of a fluid agent in accordance with an embodiment of the present disclosure.
Figure 5:
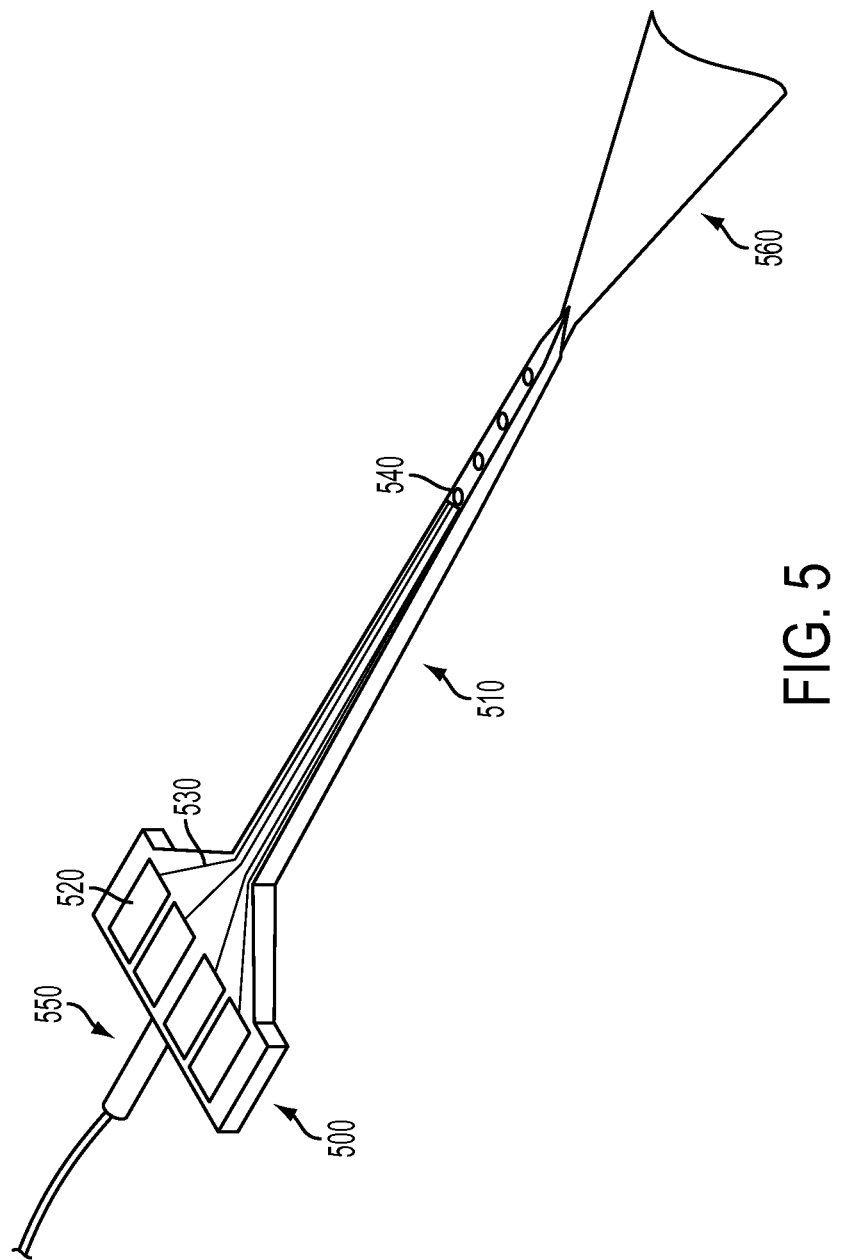
FIG. 5 is a perspective view of a micro-molded electrode adapted for delivery of electromagnetic radiation in accordance with an embodiment of the present disclosure.

Similarly, a channel or channels can be formed within the MME that are adapted to deliver at least on active agent, as shown in FIG. 4. Additionally, a channel or channels can be formed within the MME that are adapted to deliver electromagnetic radiation, as shown in FIG. 5. Channels can also be made to deliver an electrical stimulus. Combinations of such channels can also be formed within the MMEs. These channels can include valves, inlets, outlets, connections, and other suitable features to control the introduction and transmission of therapeutic agents, electrical stimuli, electromagnetic radiation, or other agents or stimuli. Channels can be formed by using sacrificial material in the shape of the channel which is oriented within the shaft through sequential deposition of structural material, sacrificial material, and additional structural material. Other approaches to forming such channels can include using lithography and etching the channel material selectively. Using material such as PEG polymer which can be dissolved in water to form channels is one example of using a sacrificial material.

Referring now to FIG. 1E, an optional coating 190 can be applied to the top side of the MME and at least one trace 150. The coating 190 can be applied using any suitable technique such as, but not limited to, lithography, spin-coating, chemical vapor deposition, atomic layer deposition, sputtering, e-beam evaporation technique, and the like. In one aspect the coating 190 is applied using standard lithography. The coating 190 can act as an insulative coating and biological barrier to protect the MME. Hence, any material suitable for insulating the MME, protecting it from biological fluids, or both can be used for the coating material. In one aspect, the coating material can include parylene-C, polyimide, polyurethane, benzocyclobutene (BCB), polymethyl methacrylate (PMMA), polydimethylsiloxane (PDMS), glass, or mixtures thereof. In one specific aspect, the coating material can include parylene-C.

Figure 1F:
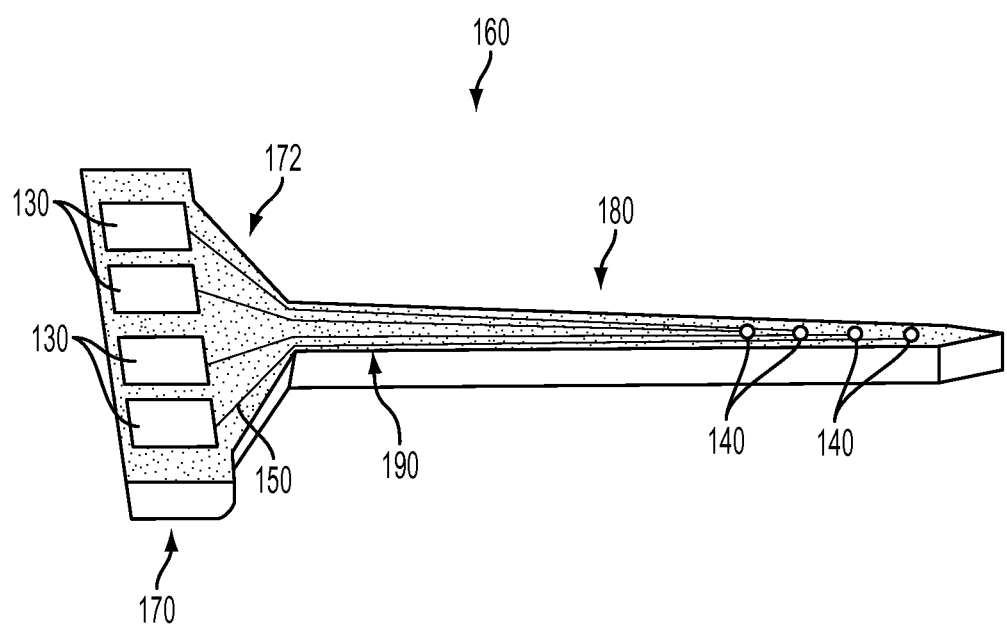
FIG. 1F is a perspective view of a micro-molded electrode released from the mold in accordance with an embodiment of the present disclosure.

As shown in FIG. 1F, the final MME 160 can be removed from the mold substrate 100. The final MME 160 can be removed by any suitable method. In one aspect, the final MME can be removed using a suitable etching technique. The final MME 160 can be removed from the mold substrate 100 by carving, etching, burning, or any other suitable technique. In one aspect, the mold substrate can be flipped and etched away to remove the MME. The wafer can be flipped and aligned by front to back aligner. In one further aspect, the etching technique can include deep reactive ion etching. Once removed from the mold substrate, the final MME 160 can also be coated on surfaces exposed by the removal of the mold substrate to further insulate the electrode, protect it from biological fluids, or both. In one alternative aspect, the coating layer can be deposited first, then the conductive material can be deposited on top of the coating, followed by deposition of the structural material. As described previously, the final MME 160 can have rounded edges. In one aspect, lower edges can be rounded by controlling the process parameters during deep reactive ion etching (DRIE). The upper edges can be rounded by controlling the polishing and grinding process for structural materials such as glass. With respect to polymeric structural materials, such rounding of edges can be done by using etching such as grey lithography.

In another embodiment, a micro-molded electrode (MME) is described. A micro-molded electrode having a base tapering to at least one shaft can include an electrode substrate with multiple individually addressable sensors on at least one side of the electrode substrate. Each individually addressable sensor can include a bonding pad at the base of the electrode electrically connected to an active site on the shaft of the electrode via an electrically conductive trace. The electrode can also have an active site on at least two sides of the electrode; and a coating covering a first side of the electrode including at least one trace.

The electrode substrate is the MME body to which or upon which the individually addressable sensors are coupled, deposited, or otherwise connected. The electrode substrate can be made of any suitable structural material as previously described. Such support materials can include, but are not limited to, silicon, aluminum, alumina, glass, quartz, steel, acrylics, silicon on insulator materials, polymeric materials such as parylene-C, polydimethylsiloxane (PDMS), and poly(methyl methacrylate) (PMMA), epoxy-based negative resist materials, such as SU8, ceramics, such as silicon carbide and tungsten carbide, and zinc oxide, and combinations thereof. In one specific aspect, the electrode substrate can be formed from a structural material that includes glass.

The MME can further include, as part of the electrode substrate, a structural support member oriented between the multiple individually addressable sensors and the substrate. The structural support member can comprise any materials that allow stiffening of the MME such that the MME can withstand insertion into the targeted tissue. In one aspect, the structural support member can include silicone, glass, steel, quartz, titanium, polymeric materials such as polypropylene, polyethylene, and other suitable polymeric materials, any other suitable support material, and combinations thereof. In one aspect, the structural member can comprise glass. While the structural support member is generally present to provide a strengthening of the electrode shaft, in one embodiment, the structural support member substantially covers the first side. In one aspect, the structural support member can cover at least a portion of the first side from the base of the electrode along the shaft of the electrode to a tip of the electrode. As such, the structural support material need not cover an entire side of the electrode but can be selectively placed to provide the desired strengthening or stiffening of the electrode as needed.

Generally, the electrode substrate can have various geometries and dimensions as desired. Specific geometries of the base, shaft, segments of the base, segments of the shaft, and combinations thereof can include any desired geometrical shape; e.g., curved, flat, square, triangular, oval, conical, etc. In one embodiment, as illustrated in FIG. 1F, the electrode can have a base 170 with a rectangular segment 172 and a tapering needle shaft segment 180. The shaft can have a gradually tapered shape to facilitate insertion of the MME and also having a rounded cross sectional shape to avoid the problem of sharp edges, providing for a cleaner, safer insertion of the MME with reduced tissue damage. In one aspect, the electrode can have a semi-conical shaft. Such geometries can extend from along the entire shaft or along a portion thereof. Furthermore, the electrodes can have any desired dimension. In one embodiment, the electrode can have a high aspect ratio. As used herein, "high aspect ratio" refers to an electrode having a length that is at least 10 times greater than its width, and most often from about 2 to about 6 times greater.

The individually addressable sensors can be any suitable sensor or sensor type for an MME. For example, the sensor can measure pH, oxygen, chemicals around the implant, or the like. Typically, the sensor can measure tissue health. In some aspects, the device can include a self measuring sensor which can test whether the MMA (device) is functioning. One such type of sensor is an impedance measurement sensor using inter-digitated electrodes. The present MMEs can include individual bonding sites connected to individual active sites by traces thereby providing an MME having a plurality of sensors which are individually addressable. The present MMEs can include active sites which are also in plane with the bonding pads. However, the bonding pads need not be in plane with the active sites. Any suitable conductive material can be used to form an individually addressable sensor of the MME. In one aspect, platinum, gold, copper, titanium, silver, conductive polymers, iridium, aluminum, and combinations thereof can be used as the conductive material. In one specific aspect, platinum can be used.

As noted previously, the micro-molded electrode can have active sites on at least two sides of the MME. Active sites on either side of the MME can be connected to bonding pads on either side of the MME through a variety of configurations. However, a bonding pad can be located on at least one side of the MME. In one aspect, at least one bonding pad can be connected to an active site on an opposite or adjacent side of the MME. This can be accomplished by providing a channel from one side of the MME to an opposite or adjacent side, the channel containing sufficient conductive material to form an electrically conductive trace or segment of an electrically conductive trace that electrically connects the bonding pad to the active site or conductive trace on the opposite or adjacent side of the MME. The channel can penetrate through the MME or it can be formed entirely on the periphery of the MME. In another aspect, at least one bonding pad can be deposited on at least two sides of the MME. The bonding pads can be electrically connected to active sites on the same side or on opposite or adjacent sides to the sides where the bonding pads are located.

The coating of the MME can cover a first side of the MME, including at least one trace. The coating can include any suitable material to provide electrical insulation, protection from biological fluids, combinations thereof, or to meet any other suitable design considerations. The coating can include a single layer or multiple layers where each layer can include a single coating material or a mixture of coating materials. In one aspect, the coating can include parylene-C, polyimide, polyurethane, BCB, alumina, hydrogels, or combinations thereof. In one specific aspect, two coating layers can be used where one layer is alumina and the second layer is parylene-C. However, each layer could include mixtures of both alumina and parylene-C. The ratios of each material in each layer can be the same or they can be adjusted, depending on the intended use of the MME.

Parylene C is chemically inert and has a low dielectric constant ($\varepsilon_r$=3.15). It has low water vapor transmission rate (WVTR) of 0.2 (g·mm)/(m$^2$·day), high resistivity (~$10^{15}$ Ω-cm) and has a USP class VI biocompatibility. Another attractive characteristic is the ability to deposit conformal and pin-hole free films at room temperature. Parylene C is also an excellent ion barrier, which is useful for implants exposed to physiological environment. This is also likely to prevent or reduce corrosion since ions have to be transported during corrosion reactions. Failure of Parylene C coating has been reported due to moisture permeation and is dramatically exacerbated by interface contamination. Another well-known issue with Parylene C is it has poor adhesion to inorganic and metal substrate materials. Moisture condensation on contaminants at the interface can also cause delamination of Parylene films. $Al_2O_3$ films deposited by atomic layer deposited (ALD) can also act as an excellent moisture barrier with WVTR at the order of ~$10^{-10}$ (g·mm)/(m$^2$·day), for preventing the degradation of implants. The biocompatibility of $Al_2O_3$ is comparable to that of corrosion resistant metals like titanium. ALD $Al_2O_3$ is also superior compared with films generated by other deposition techniques such as sputtered $Al_2O_3$ in terms of moisture barrier because it is denser and pin-hole free. Liquid water is known to slowly corrode $Al_2O_3$ thin films, mostly likely due to the incorporation of hydrogen in the form of OH groups in the film. Therefore, $Al_2O_3$ alone may not be suitable for encapsulation of biomedical implants directly exposed to physiological environment. However, combining $Al_2O_3$ and Parylene C can be desirable as $Al_2O_3$ works as an inner moisture barrier and Parylene works as an external ion barrier, preventing contact of $Al_2O_3$ with liquid water, and slowing the kinetics of alumina corrosion.

The MMEs disclosed herein generally comprise a single shaft or multiple shaft configuration having various individual addressable channels. In one embodiment, the electrode can be a single shaft electrode, as illustrated in FIG. 1F. In one aspect, the single shaft electrode can have 1 to 16 channels. In one aspect the shaft can be adapted for insertion into nervous tissue or other suitable tissue.

In another embodiment, the electrode can be a multiple shaft electrode, as illustrated in FIG. 2. FIG. 2 depicts an MME with a single base 200 with multiple shafts 210 extended therefrom. Though FIG. 2 depicts an MME with three shafts 210, there can be more or less than three. In one aspect, the multiple shaft electrode can have 4 to 128 channels.

Although penetrating electrodes can be formed, surface or planar electrodes can also be used. For example, as illustrated in FIG. 3, the shaft 310 can extend from the base 300 and can be adapted to have a disk 320 associated therewith for topical monitoring of nervous or other suitable tissue. The bonding bads 350 are electrically connected to active sites 330 on the disc 320 via the conductive traces 340. In this case, multiple active sites can be distributed across the disk to provide increased two-dimensional coverage. The individual traces track parallel along a common shaft and then branch out across the disk.

While the present electrodes can be used in traditional electrical stimulation applications, the electrodes can be configured for use in other applications including delivery of an active agent, an electrical stimulus, electromagnetic radiation, and combinations thereof. In one embodiment, the electrode can further comprise a channel from the base of the electrode to a tip of the electrode. In one aspect, the channel can be adapted to deliver an active agent, as shown in FIG. 4. FIG. 4 illustrates an embodiment of an MME that has a base 400 and a shaft 410 extending therefrom. Bonding pads 420 are located at the base 400 and are electrically connected to active sites 440 on the shaft 410 via conductive traces 430. Additionally, a therapeutic agent delivery conduit 460 is fluidly connected to the base 400 in order to conduct the agent 450 through an inner channel and out of the tip of the shaft 410. In one specific aspect, the active agent can be a medicinal drug. In another aspect, the channel can be configured for delivery of an electrical stimulus. Thus, in some aspects, the device can provide active agent delivery contemporaneously with and spatially adjacent to electrical stimulus.

In another aspect, the channel can be configured for delivery of electromagnetic radiation, as shown in FIG. 5. FIG. 5 illustrates an embodiment that has a bonding pads 520 at the base 500 that are electrically connected to active sites 540 on the shaft 510 via conductive traces 530. Additionally, a source 550 of electromagnetic radiation 560 is optically connected at the base 500 in order to transmit electromagnetic radiation 560 through the MME. Further, magnetic stimulation can be applied using these devices. Given these additional delivery aspects, the present electrodes can further comprise materials for facilitating such deliveries. For example, in one aspect, the channel can further comprise a coating therein for minimizing interactions of the active agent with materials used to manufacture the electrode. In another aspect, the channel can include conductive materials for facilitating the delivery of an electrical stimulus. In another aspect, the channel can further comprise wave guide materials for facilitating the transmission of light through the channel. For example, reflective coatings can be used or structural materials can be chosen to have internal reflection sufficient to deliver the electromagnetic radiation. These channels can also include valves, inlets, outlets, connections, and other suitable features to control the introduction and transmission of therapeutic agents, electrical stimuli, electromagnetic radiation, or other agent or stimulus.

Figure 6A:
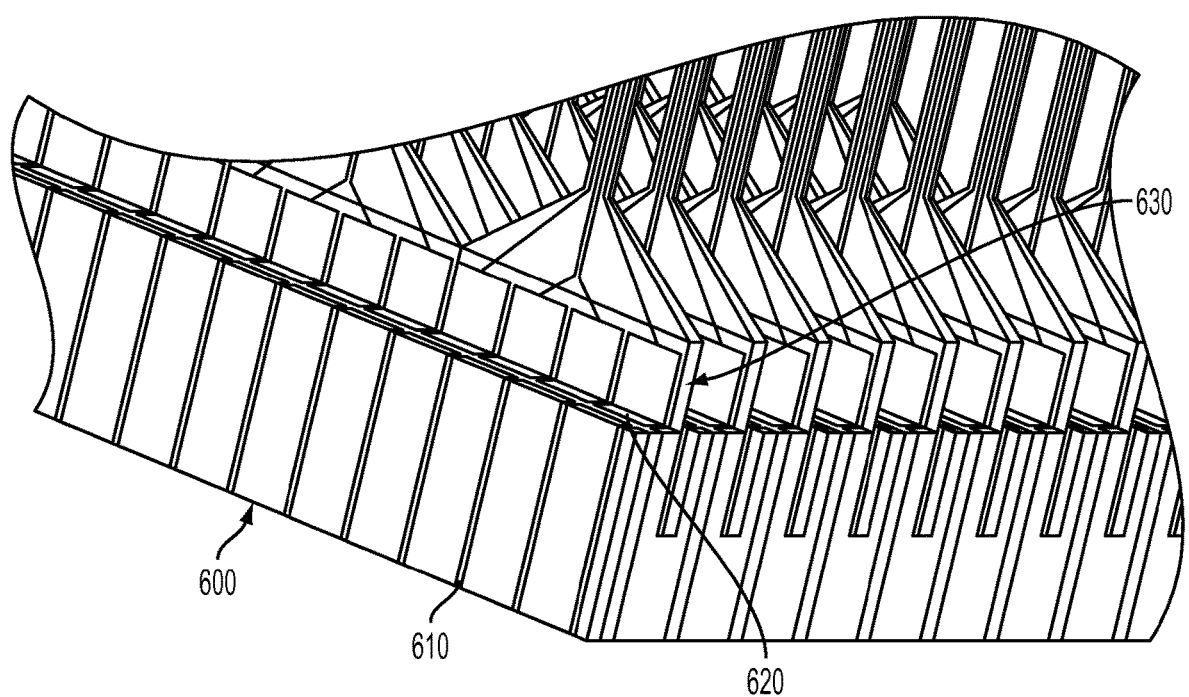
FIG. 6A is a close-up perspective view of a slotted base used in a 3D micro-molded array in accordance with an embodiment of the present disclosure.
Figure 6B:
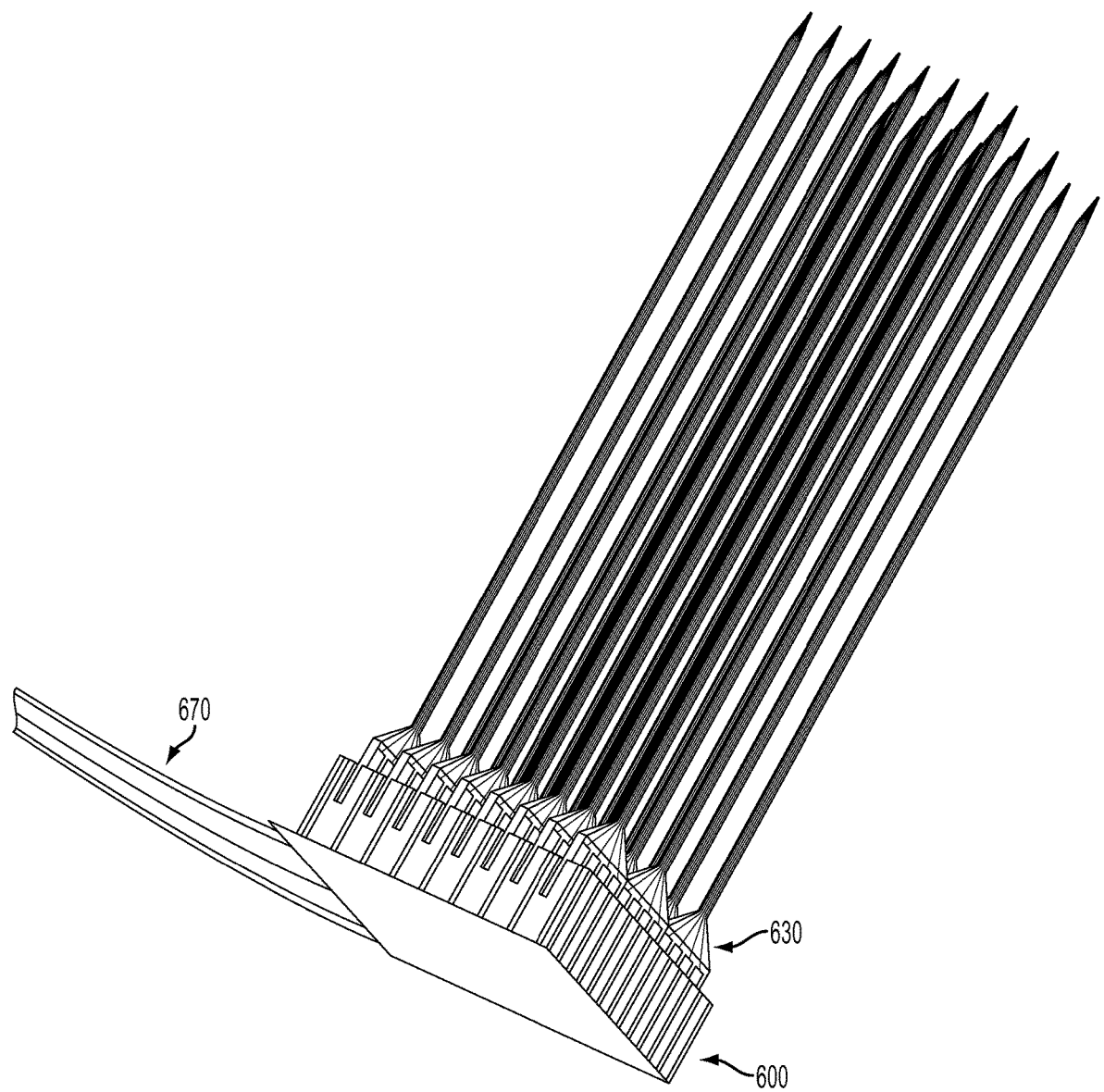
FIG. 6B is a perspective view of the 3D micro-molded array of FIG. 6A.
Figure 6C:
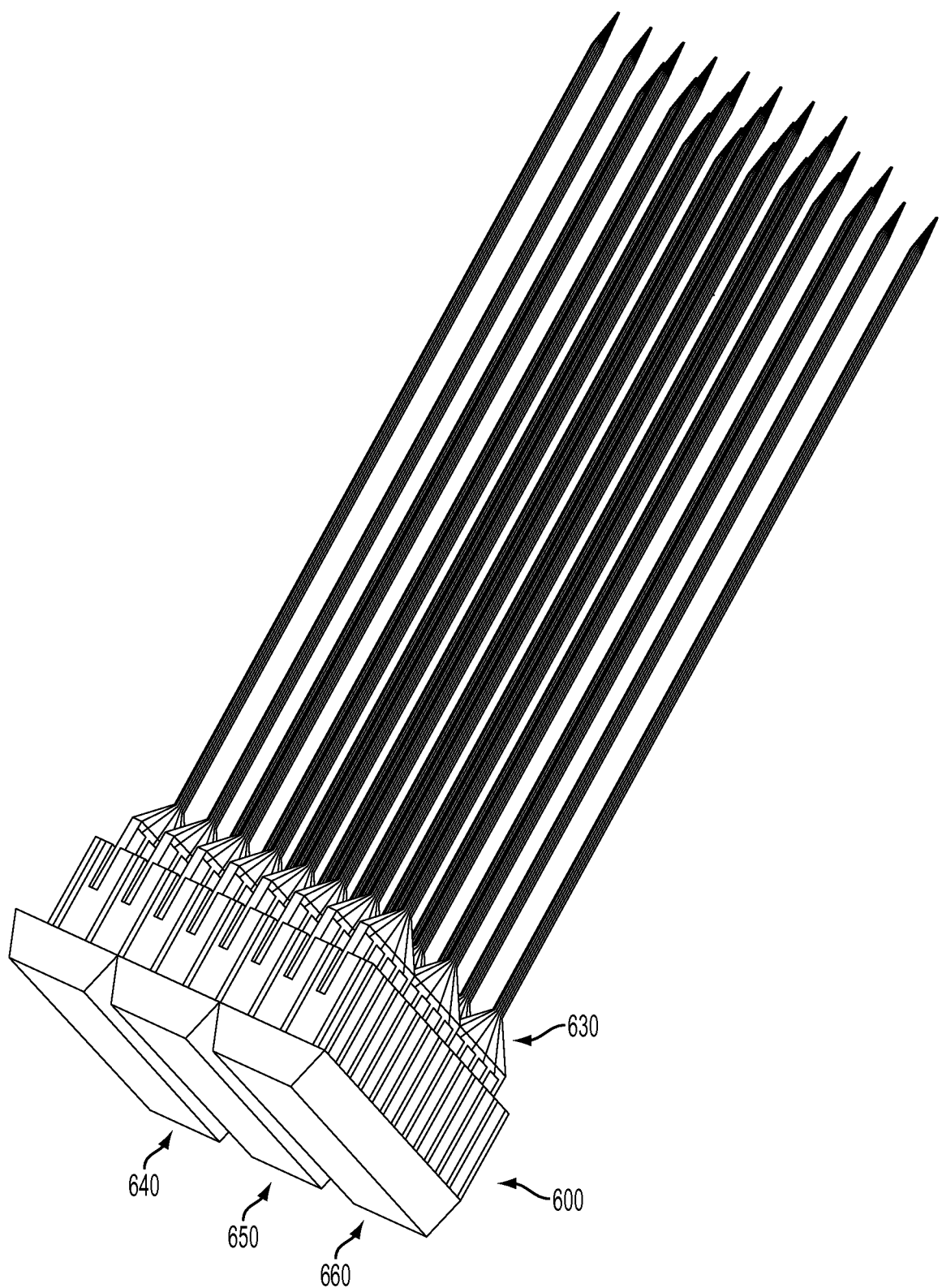
FIG. 6C is a perspective view of a 3D micro-molded array adapted for wireless communication in accordance with an embodiment of the present disclosure.

Multiple sets of the present electrodes can be used in conjunction to form an array. As such, in one embodiment, a micro-molded array can comprise a plurality of MMEs as described herein. The micro-molded array can include a plurality of MMEs oriented in a 2D array. Additionally, in one embodiment, the plurality of electrodes can be oriented in a 3D array, as illustrated in FIGS. 6A-6C. Such an array can comprise a slotted base, the slotted base having a plurality of slots configured to receive the bases of the plurality of MMEs or 2D arrays. In one aspect, the slotted base can be adapted to receive a plurality of individual MMEs. In another aspect, the slotted base can be adapted to receive a plurality of 2D arrays.

As illustrated in FIG. 6A, in one aspect the slotted base 600 can have conductive connections 620 that are adapted to electrically interact with the bonding pads on the MME. This allows the slotted base 600 to receive electrical signals from each of the MMEs 630 connected to the slotted base 600. The slotted base 600 can have a plurality of slots that are adapted to receive a plurality of MMEs 630. A conductive connection 620 can include any suitable conductive material. In one aspect, the conductive connection 620 can include platinum, gold, copper, titanium, silver, conductive polymers, iridium, aluminum, and combinations thereof. In one aspect, the conductive connection 620 can include the same conductive material as that used for the MME. In one specific aspect, the conductive connection 620 can include platinum.

Furthermore, as shown in FIG. 6A, the slotted base 600 can include insulation barriers 610 between the conductive connections 620. The insulation barriers 610 can include any suitable insulation material. In one aspect, the insulation material can include parylene-C, polyimide, polyurethane, benzocyclobutene (BCB), polymethyl methacrylate (PMMA), polydimethylsiloxane (PDMS), glass, or mixtures thereof. However, there are many other insulators that can be used in the insulation barrier 610 that are known by those skilled in the art, and any such materials are contemplated as useful in the current technology.

As depicted in FIG. 6B, the slotted base 600 can be connected to a transmission cable 670. The transmission cable can be coupled to a computer or other electronic device, including a wearable device that is adapted to store, process, or transmit data received via the electrode, or combinations thereof. The data can be stored locally, transmitted to a remote database, provide a biofeedback signal, signal administration of a therapeutic agent, electrical stimulus, electromagnetic radiation, combinations thereof, or other suitable agent or stimulus. In one aspect, as depicted in FIG. 6C, the slotted base 600 can be adapted to communicate wirelessly. The wireless communication components can include a power module 640, a processing module 650, and a transceiver module 660 coupled to or formed on the slotted base 600. The power module 640 can be adapted to electrically power the processing module 650, the transceiver module 660, and the sensors on the MMEs 630.

General types of electrodes that are contemplated for use and manufacturing of include barbed electrodes, flexible electrodes utilizing flexible substrate, surface electrodes, penetrating electrodes, drug delivering electrodes, light delivering electrodes, electrical-stimulus delivering electrodes, and any other suitable electrode.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiment(s) of the invention. It will be apparent to those of ordinary skill in the art that numerous modifications can be made without departing from the principles and concepts of the invention as set forth in the claims.

What is claimed is:

1. A method of manufacturing a micro-molded electrode having multiple individually addressable sensors along a shaft of the micro-molded electrode, comprising:
   modifying a mold substrate to form a recess therein on a first surface of the mold substrate, the recess defining a perimeter of the micro-molded electrode;
   depositing a structural material within the recess to form the micro-molded electrode, the structural material forming a base and the shaft of a finished micro-electrode and the shaft including a tapered microneedle shape;
   depositing a conductive material at specific locations on the structural material such that the conductive material forms the multiple individually addressable sensors along the shaft of each of the micro-molded electrode, each sensor comprising a bonding pad at the base of the micro-molded electrode electrically connected to an active site on the shaft of the micro-molded electrode via an electrically conductive trace, the micro-molded electrode having an active site on at least two sides of the micro-molded electrode;
   coating a top side of the micro-molded electrode and at least one trace with a coating material; and
   removing the mold substrate outside the perimeter.

2. The method of claim 1, further comprising depositing the structural material within the recess before the deposition of the conductive material.

3. The method of claim 2, further comprising polishing the first surface of the mold substrate after deposition of the structural material.

4. The method of claim 2, wherein the structural material is heated to form a solid cohesive structural material.

5. The method of claim 2, wherein the structural material is selected from the group consisting of silicon, aluminum, alumina, glass, quartz, steel, epoxy-based negative resist materials, acrylics, silicon on insulator (SOI), and combinations thereof.

6. The method of claim 1, wherein the coating material includes parylene-C, polyimide, polyurethane, benzocyclobutene (BCB), polymethyl methacrylate (PMMA), polydimethylsiloxane (PDMS), glass, or mixtures thereof.

7. The method of claim 1, further comprising coating surfaces of the micro-molded electrode exposed by the removal of the substrate outside the perimeter.

8. The method of claim 1, wherein modifying comprises etching the mold substrate.

9. The method of claim 8, wherein etching comprises deep reactive ion etching.

10. The method of claim 1, wherein depositing the conductive material includes a lithography process to form the bond pads, the active sites, and the electrically conductive traces.

11. The method of claim 1, wherein the coating includes a lithography process using the coating material.

12. The method of claim 1, wherein removing comprises etching the mold substrate.

13. The method of claim 12, wherein etching comprises deep reactive ion etching.

14. The method of claim 1, further comprising forming a channel within the micro-molded electrode adapted to deliver at least one active agent.

15. The method of claim 1, further comprising forming a channel within the micro-molded electrode which is adapted to deliver an electromagnetic radiation.

16. The method of claim 1, further comprising coupling a plurality of the micro-molded electrodes to a slotted base, the slotted base having a plurality of slots which receive the micro-molded electrodes.

17. The method of claim 16, further comprising forming a power module, a processing module, and a transceiver module on the slotted base, wherein the power module electrically powers the processing module, the transceiver module and the sensors.

* * * * *